United States Patent
Brunnberg et al.

(10) Patent No.: US 10,525,201 B2
(45) Date of Patent: Jan. 7, 2020

(54) MEDICAMENT DELIVERY DEVICE

(71) Applicant: Carebay Europe Ltd, Swatar (MT)

(72) Inventors: Lennart Brunnberg, Tyresö (SE); Stephan Olson, Danderyd (SE)

(73) Assignee: SHL MEDICAL AG, Zug (CH)

( * ) Notice: Subject to any disclaimer, the term of this patent is extended or adjusted under 35 U.S.C. 154(b) by 354 days.

(21) Appl. No.: 14/404,542

(22) PCT Filed: May 22, 2013

(86) PCT No.: PCT/EP2013/060466
§ 371 (c)(1),
(2) Date: Nov. 28, 2014

(87) PCT Pub. No.: WO2013/178512
PCT Pub. Date: Dec. 5, 2013

(65) Prior Publication Data
US 2015/0209517 A1    Jul. 30, 2015

Related U.S. Application Data

(60) Provisional application No. 61/653,574, filed on May 31, 2012.

(30) Foreign Application Priority Data

May 31, 2012  (SE) ...................................... 1250567

(51) Int. Cl.
*A61M 5/20*   (2006.01)
*A61M 5/315*  (2006.01)

(52) U.S. Cl.
CPC ........ *A61M 5/2033* (2013.01); *A61M 5/3157* (2013.01); *A61M 2005/206* (2013.01);
(Continued)

(58) Field of Classification Search
CPC .. A61M 2005/2013; A61M 2005/2086; A61M 5/2033; A61M 5/3157
See application file for complete search history.

(56) References Cited

FOREIGN PATENT DOCUMENTS

WO    WO 2005115516 A1 * 12/2005 .......... A61M 5/2033
WO    2011/043714 A1    4/2011
(Continued)

OTHER PUBLICATIONS

EPO, Int'l Search Report in PCT/EP2013/060466, dated Jul. 25, 2013.
EPO, Written Opinion in PCT/EP2013/060466, dated Jul. 25, 2013.

*Primary Examiner* — Deanna K Hall
(74) *Attorney, Agent, or Firm* — McDonnell Boehnen Hulbert & Berghoff LLP

(57) ABSTRACT

A medicament delivery device has a drive mechanism that includes a first resilient member and a delay plunger rod assembly that includes a proximal plunger, a distal plunger, a chamber formed between the proximal and the distal plungers, an aperture, and a delay device in the chamber. The distal plunger is positioned and configured in relation to a hold and release mechanism such that, as the drive mechanism exerts a pressure on the medicament container, the distal plunger acts against the delay device, delaying a release of a signal generating member after a release of the drive mechanism to allow remaining contents of medicament in a medicament container to be completely expelled before the signal generating member is released.

18 Claims, 7 Drawing Sheets

(52) U.S. Cl.
CPC ............... *A61M 2005/2013* (2013.01); *A61M 2005/2086* (2013.01)

(56) References Cited

FOREIGN PATENT DOCUMENTS

| | | | | |
|---|---|---|---|---|
| WO | 2011/123024 A1 | 10/2011 | | |
| WO | WO 2011123024 A1 * | 10/2011 | .......... | A61M 5/2033 |
| WO | 2012/025639 A1 | 3/2012 | | |
| WO | WO 2012025639 A1 * | 3/2012 | ............ | A61M 5/001 |

* cited by examiner

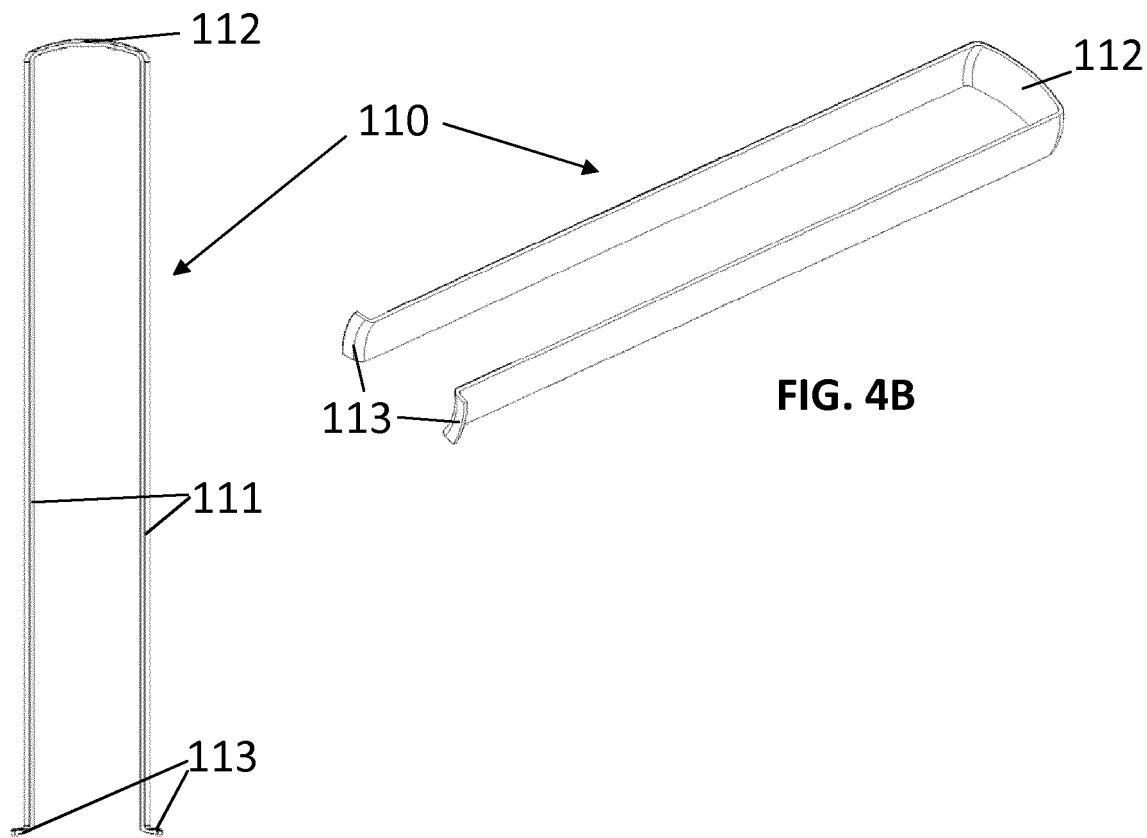
FIG. 4B
FIG. 4A
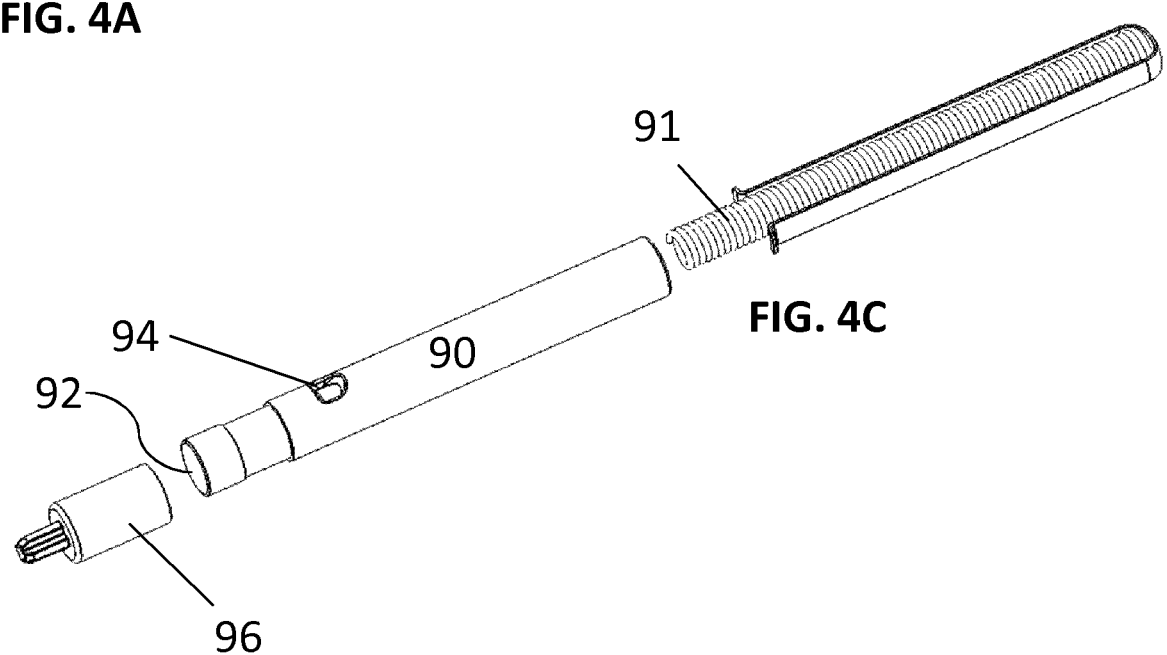
FIG. 4C

MEDICAMENT DELIVERY DEVICE

TECHNICAL FIELD

The present invention relates to a medicament delivery device and in particular to an accurate and reliable automatic medicament delivery device providing a complete delivery of medicament followed by a reliable audible and/or tactile and/or visible confirmation to the user that the delivery has been completed.

BACKGROUND

Many medicament delivery devices are developed for self-administration, i.e. a user performs the medicament delivery her-, or himself. This requires a medicament delivery device which is reliable, accurate, safe and easy to use. In order to meet these requirements, the risk of human errors must be minimized, the number of actions needed to be performed in order to receive a dose need to be reduced and the device must be intuitive to use. Thus, in order to minimize the risk of human errors, it is desirable to have a device that accurately provides a user with confirmation that he/she has received a complete dose of medicament.

Medicament delivery devices such as injection devices providing automatic or manual delivery member insertion, automatic injection of a medicament, automatic delivery member retraction or automatic covering of the delivery member are known in the art. Though these injection devices known in the art have a major number of advantages, there is always room for improvement. For example, a device that provides both a complete delivery of medicament and release of a member that produces a reliable audible and/or tactile and/or visible confirmation to the user that the delivery has been completed has hitherto been required to be manufactured to extremely tight tolerances. For example, a release of a member that produces a reliable audible and/or tactile and/or visible confirmation to the user that the delivery has been completed is disclosed in WO2011043714A1. The release of a member that produces a reliable audible and/or tactile and/or visible confirmation to the user that the delivery has been completed is accomplished by disengaging a plunger rod from a second activator member once the plunger rod has terminated its displacement for delivering the medicament. The termination of the plunger rod displacement and the disengaging of the plunger rod from the second activator member must occur simultaneously if both a complete delivery of a medicament and a release of the second activator member which produces the reliable audible and/or tactile and/or visible confirmation to the user that the delivery has been completed are to be accomplished. Thus, in WO2011043714A1 there is only one mechanical position that is used to activate the release of the second activation member at the point where it is expected that the plunger displacement will terminate. The precision of the timing of the termination of plunger displacement and disengagement of the plunger from the second activation member relies on the manufacturing and assembly dimensions of the parts of the device and thus the tolerances play an important role in the proper functioning of the device. Thus, in order to compensate for component tolerances a signal generating member needs to be released before the plunger displacement has terminated. A user may then be prone to remove the device from the delivery site causing the medicament to not be completely delivery to the patient. In order to ensure a complete and accurate delivery of a medicament all the parts or components of the device must be manufactured to very tight tolerances leading to high manufacturing and assembling costs. Even the medicament container must be manufactured with such tight tolerances in mind, which is rare. Thus, it would be an improvement in the art to provide a medicament delivery device that can be manufactured and assembled having reliable effects such as a complete delivery of a medicament followed by an audible and/or tactile and/or visible confirmation to the user that the delivery has been completed.

SUMMARY OF THE INVENTION

The object of the present invention is to provide an accurate and reliable automatic medicament delivery device providing a complete delivery of medicament followed by a reliable audible and/or tactile and/or visible confirmation to the user that the delivery has been completed. This is achieved by a medicament delivery device comprising: a housing having a distal and an proximal end, said housing being adapted to receive a medicament container with a delivery member or with a connectable delivery member for delivery of a medicament; a drive mechanism arranged to act on the medicament container for providing automatic delivery of the medicament; a hold and release mechanism interactively connected to the drive mechanism for holding the drive mechanism in a pre-tensioned state; a biased delivery member cover positioned at least partially and axially movable within the housing, said biased delivery member cover being interactively connected to the hold and release mechanism, such that when said biased delivery member cover is pressed against a delivery site said hold and release mechanism releases the drive mechanism from the pre-tensioned state; a signal generating member releasibly connected to said hold and release mechanism and interactively arranged to said drive mechanism for generating an audible and/or tactile and/or visual signal indicating that the medicament has been completely delivered; wherein the drive mechanism comprises a first resilient member and a delay plunger rod assembly; wherein the delay plunger rod assembly comprises a proximal plunger, a distal plunger, a chamber formed between the proximal and the distal plungers, and aperture, and delay means contained within the chamber; the distal plunger being positioned and configured in relation to the hold and release mechanism such that, as the drive mechanism exerts a pressure on the medicament container, the distal plunger acts against the delay means whereby the release of the signal generating member is delayed after the release of the drive mechanism to allow the remaining contents of medicament in the medicament container to be completely expelled before the signal generating member is released.

According to another aspect of the invention, the delay means is a high-viscous fluid or an expanded plastic.

According to a further aspect of the invention, the distal plunger is positioned at least partially within or around the proximal plunger such that said distal plunger is axially movable in relation to said proximal plunger.

According to a yet another aspect of the invention, wherein the aperture is positioned on a wall surface of the distal plunger, preferably on a proximal end wall of the distal plunger or on a wall surface of the proximal plunger or is a gap between the distal and proximal plungers.

According to a further aspect of the invention, the pressure exerted on the container is directly exerted on the stopper and the first resilient member is pre-tensioned arranged within the distal plunger.

According to another aspect of the invention, the hold and release mechanism comprises a tubular extension part fixedly connected to the distal end of the housing and a tubular operation member interactively connected to tubular extension part and to the biased delivery member cover.

According to a yet another aspect of the invention, the tubular operation member comprises guide means interactively connected to guide following means of the biased delivery member cover and releasing means interactively connectable to holding means of the tubular extension part.

According to yet another aspect of the invention, the distal plunger is positioned at least partially and axially movable within the tubular extension part and wherein the distal plunger comprises engaging means interactively connected to the holding means of the tubular extension part.

According to another aspect of the invention, the signal generating member is an elongated u-shaped bracket arranged between the tubular extension part and the distal plunger rod, the signal generating member comprises a transversal wall and two longitudinally extending flexible arms provided with angled support members extending radially outward, and wherein said support members are adapted to rest on an annular proximal end of the tubular extension part when the drive mechanism is in the pre-tensioned state.

According to a further aspect of the invention, the first resilient member has a first end abutting a proximal end wall of the distal plunger and a second end abutting the transversal wall of the signal generating member.

According to yet another aspect of the invention, the transversal wall of the signal generating member is arranged at a predetermined distance D from an inner distal surface of said tubular extension part when the drive mechanism is in the pre-tensioned state.

According to yet a further aspect of the invention, the releasing means comprises a longitudinally extending groove on an inner surface of the tubular operation member and the holding means of the tubular extension part comprises a resilient tongue having a radial inward protrusion.

According to another aspect of the invention, the releasable engaging means comprises a groove or cut-out/recess on an outer surface of the distal plunger configured to receive the radial inward protrusion of the resilient tongue of the tubular extension part.

According to a further aspect of the invention, the guide means comprise at least one tracking groove on an outer surface of the tubular operation member and the guide following means comprise a radial inward extending protrusion on the distal end of the inner surface of the biased delivery member cover, such that said radial inward extending protrusion is adapted to be guided within the at least one tracking groove on the outer surface of the tubular operation member forcing the tubular operation member to rotate when the biased delivery member cover is distally moved, whereby the resilient tongue of the tubular extension part is flexed radially outwards into the longitudinally extending groove on the inner surface of the tubular operation member and the radial inwardly extended protrusion of the resilient tongue of the tubular extension part is disengaged from the groove or cut-out/recess on the outer surface of the distal plunger such that the drive mechanism is released from the pre-tensioned state.

According to yet another aspect of the invention, an audible signal is generated for confirming that the remaining contents of medicament in the medicament container is completely delivered when drive mechanism is released and the distal end of the distal plunger has passed the angled support members of the signal generating member, such that the longitudinally extending flexible arms are flexed radially inwards and thereby enabling the signal generating member to move the predetermined distance D in the distal direction by a remaining force exerted by said first resilient member, whereby the transversal wall of the signal generating member hits the inner distal surface of said tubular extension part.

According to yet a further aspect of the invention, the transversal wall of the signal generating member comprises a distally extending protrusion and the distal surface of the tubular extension part comprises a through hole, such that when the transversal wall of the signal generating member hits the inner distal surface of said tubular extension part, the distally extending protrusion passes through the through hole and extends distally a predetermined distance over the outer surface of said tubular extension part for generating a tactile signal.

According to another aspect of the invention, the distally extending protrusion has a bright and/or different colour than the rest of the device for generating a visual signal.

According to a further aspect of the invention, the aperture is positioned on a proximal end wall of the distal plunger or on a wall surface of the proximal plunger.

According to yet a further aspect of the invention, the device is an injection device and wherein the delivery member is a needle or a pen needle.

By the term automatic medicament delivery device, is herein meant a medicament delivery device adapted to deliver a medicament without a user having to press a plunger rod, but instead only by pressing a proximal part of the medicament delivery device against the delivery site or by first pressing a proximal part of the medicament delivery device against the delivery site and then pressing a button or by first pressing a button and then a proximal part of the medicament delivery device against the delivery site. The automatic medicament delivery device may provide the sequences of semi-penetration i.e. penetrating the delivery member only pressing the biased delivery member cover against a delivery site and an auto-injection followed by an automatic resetting of the biased delivery member cover wherein the user is prevented to have access to the delivery member. Further, the automatic medicament delivery device may alternatively provide the sequences of auto-penetration and an auto-injection followed by an automatic resetting of the biased delivery member cover wherein the user is prevented to have access to the delivery member.

In automatic medicament delivery device it is considered important, as mentioned above, that the patient receives a reliable confirmation that the delivery has been made, in particular when the medicament delivery device is used out of sight of the patient, e.g. such as around the waist and also on the backside of the waist and/or in the buttocks of the patient. Therefore, a signal i.e. an audible sound, and/or a tactile signal, and/or a visual signal, or a combination thereof is generated in direct temporal relationship to the physical actuation of the medicament container, in order to expel the medicament from the medicament container.

The medicament delivery device according to the present invention presents a number of advantages. There is a high degree of reliability, functionality and automation, which eliminates unnecessary components and actions for delivering a medicament, leading to a safe device that is also cheaper to manufacture and to assemble.

Also an important safety aspect is met since, during withdrawal, the biased delivery member cover is pushed out and covers the delivery member e.g. a delivery member, and also locks in the extended state, thereby preventing unintentional delivery member sticks.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which FIG. 1a-FIG. 1c shows perspective views of different components of the medicament delivery device.

FIG. 4a-FIG. 4c illustrates the signal generating member, and the components of the drive mechanism.

DETAILED DESCRIPTION

Figure 1A:
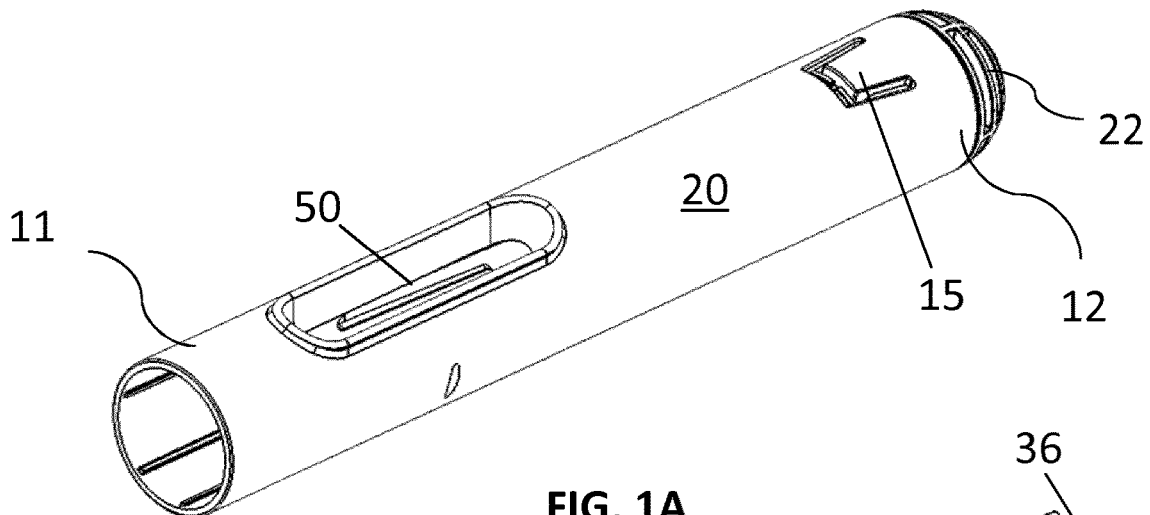

In the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

The medicament delivery device according to the present invention comprises: a housing 20 having a distal 12 and an proximal 11 end and extending along a longitudinal axis 21, said housing being adapted to receive a medicament container with a delivery member 61 or with a connectable delivery member for delivery of a medicament; a drive mechanism arranged to act on the medicament container for providing automatic delivery of the medicament; a hold and release mechanism interactively connected to the drive mechanism for holding the drive mechanism in a pre-tensioned state; a biased delivery member cover 30 positioned at least partially and axially movable within the housing, said biased delivery member cover being interactively connected to the hold and release mechanism, such that when said biased delivery member cover is pressed against a delivery site said hold and release mechanism releases the drive mechanism from the pre-tensioned state; a signal generating member 110 releasibly connected to said hold and release mechanism and interactively arranged to said drive mechanism for generating an audible and/or tactile and/or visual signal indicating that the medicament has been completely delivered; wherein the drive mechanism comprises a first resilient member 91 and delay plunger rod assembly; wherein the delay plunger rod assembly comprises a proximal plunger 96, a distal plunger 90, a chamber 95 formed between the proximal and the distal plungers, an aperture, and delay means contained within the chamber; the distal plunger being positioned and configured in relation to the hold and release mechanism such that, as the drive mechanism exerts a pressure on the medicament container, the distal plunger acts against the delay means whereby the release of the signal generating member is delayed after the release of the drive mechanism to allow the remaining contents of medicament in the medicament container to be completely expelled before the signal generating member is released.

FIG. 1a illustrates, in perspective, the housing 20 of an exemplary medicament delivery device 1. The housing 20 further comprises a protrusion (not illustrated) on its inner wall. The protrusion is adapted for receiving a guide member 36 of the biased delivery member cover 30 (see FIG. 1b). The biased delivery member cover 30 is positioned at least partially and axially movable within the housing. In an exemplary embodiment there are two protrusions (not illustrated), one on each side of the inner wall of the housing 20, and correspondingly two guide members 36 of the biased delivery member cover 30. In the illustrated embodiment, the housing 20 further comprises a container holder 50 which is coaxially arranged attached within the housing 20 for lodging a medicament container 80 (see FIG. 1c). The container holder 50 may be either fixedly connectable to the housing or axially movable in relation to the housing.

The hold and release mechanism comprises a tubular extension part 22 fixedly connected to the distal end of the housing and a tubular operation member 100 interactively connected to the tubular extension part 22 and to the biased delivery member cover 30. The tubular extension part 22 being coaxially arranged and fixedly attached to the distal end 12 of the housing preferably by a resilient tongue 15 engaging with a corresponding ledge 23 (see FIG. 5) of the tubular extension part 22.

Figure 1B:
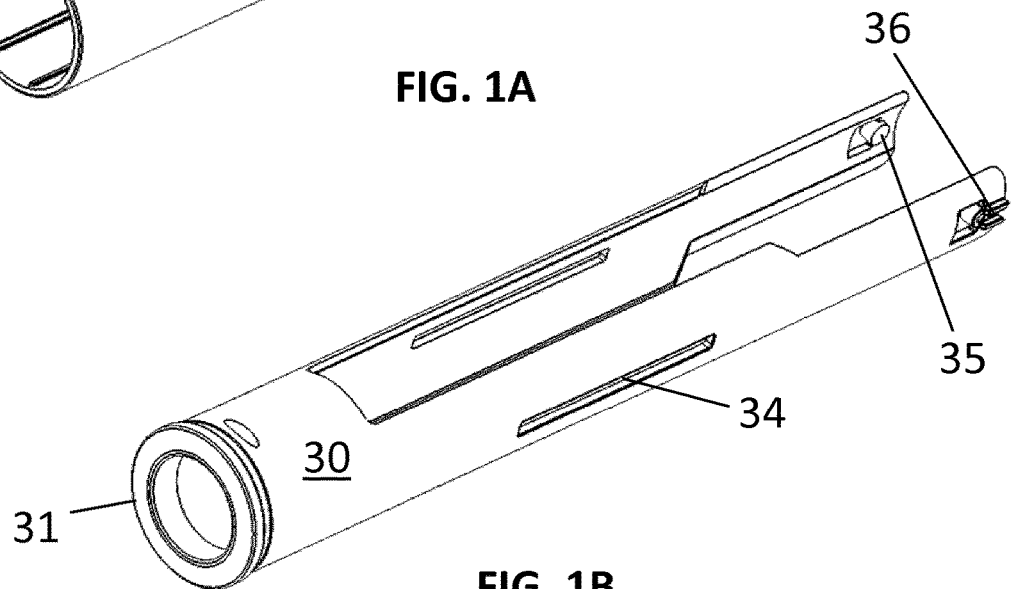

FIG. 1b illustrates the biased delivery member cover 30 of the medicament delivery device 1. The biased delivery member cover 30 having an annular contact member 31 and guide following means 35, which in an exemplary embodiment is a radial inwardly extending protrusion. In an exemplary embodiment of the invention there are two guide following means 35 which are used for activating the medicament delivery device 1 as will be described in detail below. Also illustrated is a guiding means 34 which is adapted to cooperate with a corresponding guiding rod (not shown) at the interior of the housing 20, with the purpose to prevent that the biased delivery member cover 30 may rotate in relation to the housing 20 and to allow the biased delivery member cover 30 to move in the axial direction in relation to the housing 20. In a preferred embodiment of the invention there are two guiding means 34 and correspondingly two guiding rods (not shown). According to an embodiment of the invention, a second resilient member 24 (see FIG. 1c), which in an exemplary embodiment is a tension spring, is arranged pre-tensioned between a ledge on the inner surface of the biased delivery member cover 30 and a ledge on the inner surface of the housing such that said biased delivery member cover 30 is forced towards the proximal direction for covering a delivery member 61.

Figure 1C:
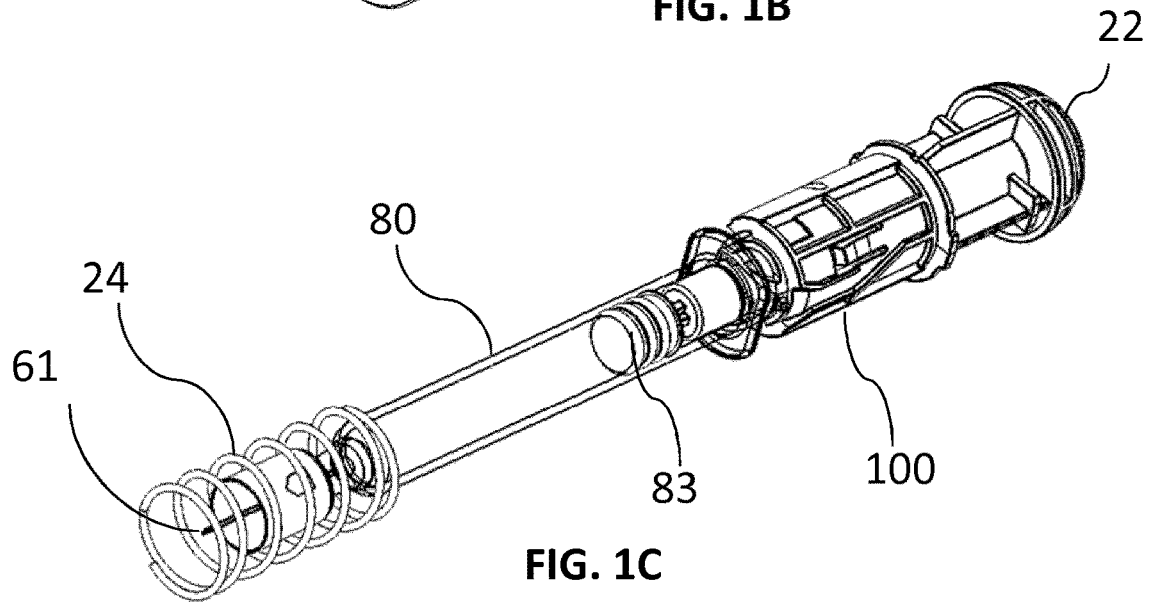

FIG. 1c illustrates the interior of the medicament delivery device 1 further comprising the second resilient member 24 arranged in relation to the biased delivery member cover 30 for forcing it in a proximal direction. The medicament container 80 comprises a predetermined volume of medicament, a stopper 83 and a delivery member 61. In an exemplary embodiment of the invention the medicament container 80 is a syringe provided with a needle as the delivery member 61, however the invention should not be limited to this, other embodiments could include a medicament cartridge having a membrane, or the like where a delivery member can be attached.

The tubular operation member 100 (see FIG. 5) comprises guide means 101, 102 interactively connected to the guide following means 35 of the biased delivery member cover 30 (see FIG. 1b). The tubular operation member 100 (see FIG. 5) further comprises releasing means 105 configured to interact with holding means 121 of the tubular extension part 22. In the illustrated embodiment, the releasing means 105 comprises a longitudinally extending groove on the inner surface of the tubular operation member 100 and the holding means 121 of the tubular extension part 22 comprises a resilient tongue having a radial inward protrusion. The tubular operation member 100 (see FIG. 5) is rotatably and coaxially arranged between the housing and a proximal part of the tubular extension part 22.

Figure 5:
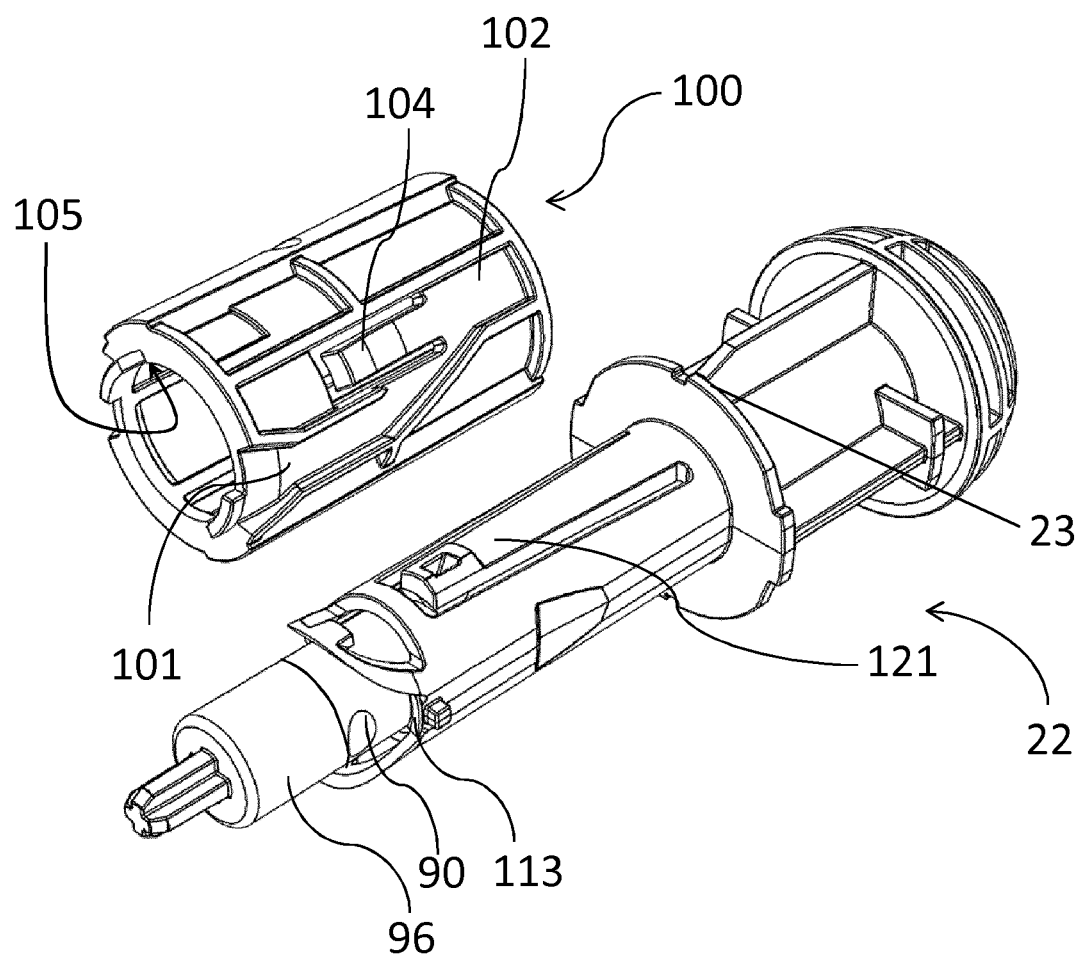
FIG. 5 shows a perspective view of a hold and release mechanism comprised in the present invention.

The distal plunger 90 comprises engaging means 94 where in the illustrated embodiments said engaging means is a groove or cut-out/recess (see FIG. 4c) to which the holding means 121 i.e. the resilient tongue with the radial inward protrusion of the tubular extension part 22, is releasably engageable (see FIG. 5). The first resilient member 91 is in an exemplary embodiment of the invention a tension spring and is is pre-tensioned arranged within the distal plunger. The proximal end of the proximal plunger 96 is in contact with the stopper 83 (see FIGS. 7 and 8).

Figure 2A:
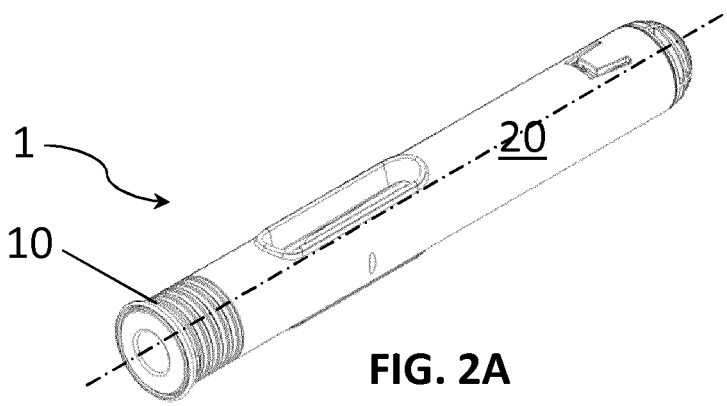
FIG. 2a-FIG. 2d shows perspective views of different states of the medicament delivery device.
Figure 2B:
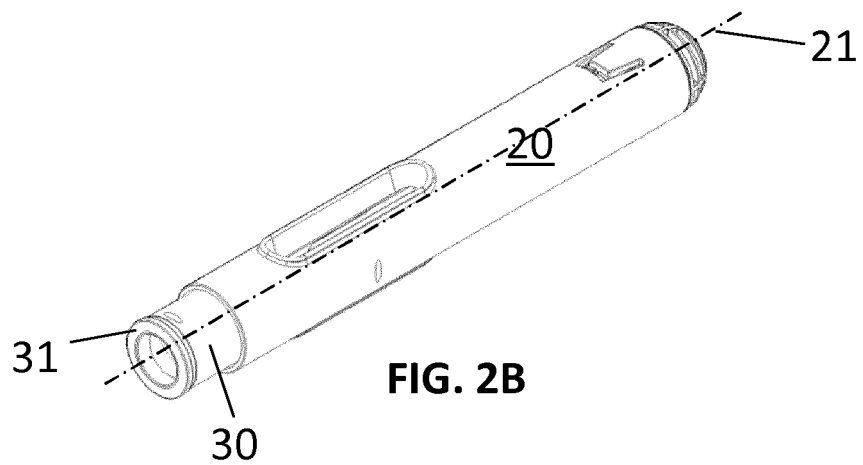
Figure 2C:
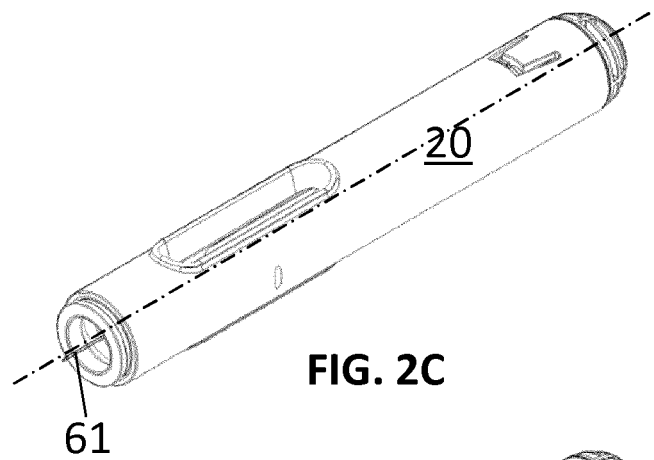
Figure 2D:
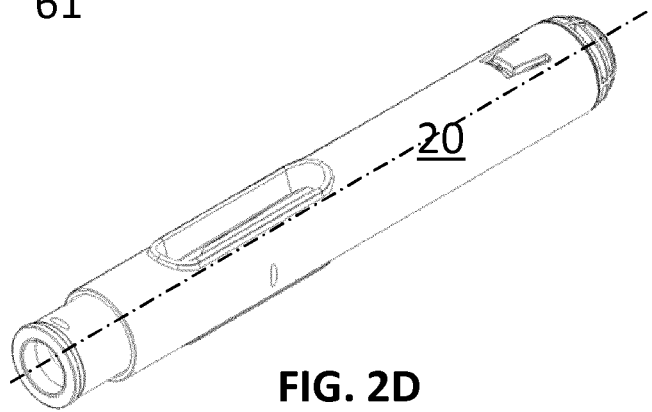

FIG. 2a-FIG. 2d show simplified perspective views of the medicament delivery device 1, where FIG. 2a illustrates an initial, non-activated, state of the medicament delivery device 1 having a cap 10. FIG. 2b shows a ready to start state of the medicament delivery device 1, where the cap 10 is removed. FIG. 2c shows the delivery state of the medicament delivery device 1 and finally FIG. 2d shows the medicament delivery device 1 in a final locked state.

FIG. 2b shows the medicament delivery device 1 when it is ready for use. When a user is about to perform a medicament delivery e.g. an injection he/she presses the proximal end, i.e. the annular contact member 31, against the delivery site e.g. an injection site. The biased delivery member cover 30 is then moved in the distal direction, in relation to the housing 20 along the longitudinal axis 21, and during the relative movement when having a medicament delivery device as an injection device, then a delivery member 61 e.g. the needle manually penetrates the skin. When the biased delivery member cover 30 is about to reach its most distal position in relation to the housing 20 the medicament delivery is performed. A medicament delivery is automatically performed when the biased delivery member cover 30, being in an activated position, is moved in a distal direction in relation to the housing 20, to a delivery state position, where the annular contact member 31 is close to the proximal end 11 of the housing 20.

FIG. 2c illustrates when the delivery is made, afterwards the user starts to remove the medicament delivery device 1 from the delivery site, thereby allowing the biased delivery member cover 30 to move in the proximal direction in relation to the housing 20, by the force exerted by the second resilient member 24 and finally reaches a final state; the locked state.

FIG. 2d illustrates the medicament delivery device 1 in its final and locked state, wherein the biased delivery member cover 30 once more is in its most proximal position, as illustrated. In this state the proximal part of the biased delivery member cover 30 fully protects the delivery member 61 and the biased delivery member cover 30 is also locked (see FIG. 1b) by the guide following means 35 in the distal end of the biased delivery member cover 30 in order to prevent unintentional interaction with the delivery member 61.

Figure 3:
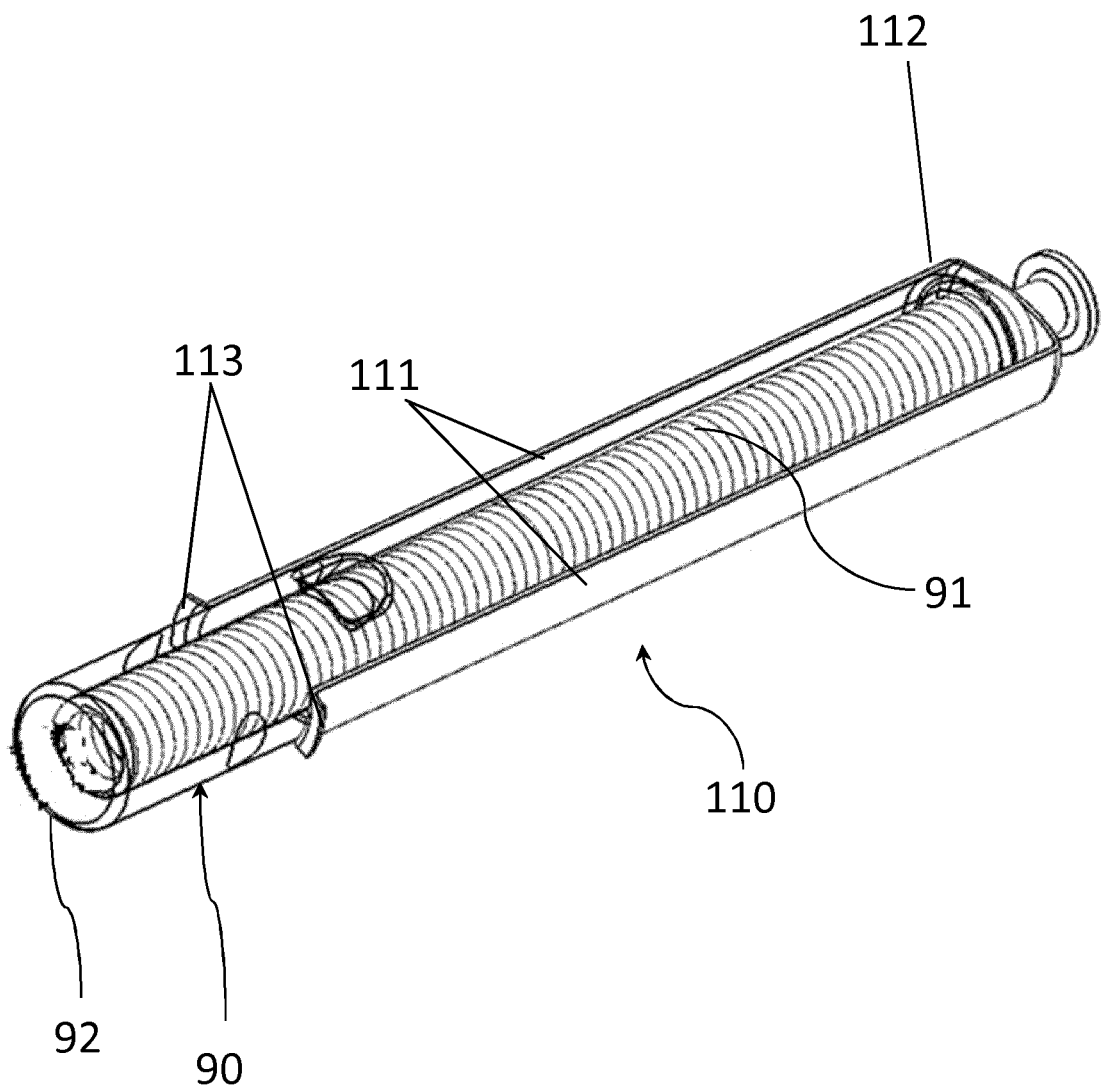
FIG. 3 illustrates a drive mechanism and a signal generating member assembly.

FIG. 3 illustrates various aspects of the signal generating member 110 and its implementation is illustrated (see also FIG. 4a-FIG. 4c). The signal generating member 110 is adapted to generate an audible and/or tactile and/or visible confirmation signal upon a performed medicament delivery, wherein the medicament delivery confirmation signal is generated when the drive mechanism changes state from a pre-tensioned state wherein the first resilient member is pre-tensioned arranged within the distal plunger and the distal plunger is engaged to the tubular extension part, to a released state wherein the distal plunger is completely released from the tubular extension part and is no longer in contact with the signal generating member.

FIG. 4a-FIG. 4c illustrate a side view and perspective views, respectively, of the signal generating member 110 according to an exemplary embodiment of the invention. In the illustrated embodiment, the signal generating member 110 is an elongated u-shaped bracket, provided with at least two elongated arms 111, directed in the proximal direction, and a lower part, a distal transversal end wall, 112 directed in the distal direction of the medicament delivery device, when arranged within the tubular extension part 22. The signal generating member 110 may be made from metal, plastic, or any combination of these materials.

FIG. 4c is a perspective, and partly exploded, view of the signal generating member 110 in relation to the delay plunger rod assembly and the first resilient member 91. The upper parts of the arms 111 are provided with angled support members 113 extending in essentially radially outward directions with regard to a longitudinal axis of the signal generating member 110. The signal generating member 110 is adapted to embrace at least a part of the distal plunger 90 and the first resilient member 91, and the support members 113 are adapted to rest on an annular surface on the proximal end of the tubular extension part 22 (see FIGS. 7 and 8) when the drive mechanism is in the pre-tensioned state. Thus the holding means 121 i.e. the resilient tongues of the tubular extension part 22 with the radial inward protrusions are engaged to the engaging means 94 i.e. the grooves or cut-outs/recesses of the distal plunger 90 wherein the first resilient member is pre-tensioned and wherein the holding means i.e. the resilient tongues of the tubular extension part 22 with the radial inward protrusions are prevented to flex radial outwards by the inner surface of the tubular operation member 100 (see FIGS. 7 and 8).

When the drive mechanism is in the pre-tensioned state, the distal end of the signal generating member 110 is arranged at a predetermined distance "D" (see FIG. 6a) from an inner distal surface of said tubular extension part 22 and when the drive mechanism is in the released state, the distal end of the signal generating member 110 is in contact with the inner distal surface of said tubular extension part 22. The audible and/or tactile and/or visible confirmation signal is generated when the distal end of the signal generating member 110 hits and contacts the inner distal surface of the tubular extension part 22 by a remaining force exerted by said first resilient member 91. Thus, during the delivery procedure, when the distal end of the distal plunger 90 passes by the supporting members 113, the arms 111 with the support members 113 are released and allowed to move in a radial inward direction, due to a pre-tension of the arms 111, enabling the signal generating member 110 to move in the distal direction by the force exerted by the first resilien member and the signal, typically an audible sound and/or a visual signal and/or a tactile signal is generated, when the signal generating member 110 hits the distal end of the tubular extension part 22. In the pre-tensioned state of the drive mechanism, the signal generating member 110 is arranged such that the arms 111 are positioned in a space along the distal plunger 90 between the distal plunger 90 and the tubular extension part 22 enclosing the distal plunger 90. The support members 113 must have an extension in the radial outward direction that exceeds the radial extension of the space between the distal plunger 90 and the inner wall of the tubular extension part 22 to secure that the signal generating member 110 is not released prior the distal plunger 90 has moved away from between the arms 111. The first resilient member 91 is pre-tensioned arranged between the distal transversal wall 112 and a proximal end wall 92 of the distal plunger. The outer distal surface of the distal transversal end wall 112 may further have a protrusion (not illustrated), adapted to be guided through an opening, typically a through-hole (also not illustrated) of the distal end wall of the tubular extension part 22 and to extend distally a predetermined distance over the outer surface of said tubular extension part 22. In an exemplary embodiment of the invention, the distally extending protrusion has a bright and/or different colour than the rest of the device for generating a visual signal. Thus, said protrusion will enable both a tactile and a visual signal when the signal generating member 110 hits the distal end of the tubular extension part 22.

FIG. 5 illustrates the tubular operation member 100, the tubular extension part 22 and the delay plunger rod assembly. In the illustrated embodiments, the guide means 101, 102 comprises at least one tracking groove on the outer surface of the tubular operation member 100. The at least one tracking groove on the outer surface of the tubular operation member 100 is configured such that said guide following means 35 i.e. the radial inwards extending protrusion on the distal end of the inner surface of the biased delivery member cover 30 is adapted to be guided within said at least one tracking groove on the outer surface of the tubular operation member 100, forcing the tubular operation member 100 to rotate when the biased delivery member cover 30 is axially moved towards the distal end.

When the tubular operation member 100 is rotated, the releasing means 105 i.e. the longitudinally extending groove on the inner surface of the tubular operation member 100 is positioned over the holding means 121 i.e. the resilient tongue with the radial inward protrusion of the tubular extension part 22, allowing the resilient tongue to flex radially outward such that its radial inward protrusion is disengaged from the engaging means 94 i.e. the grooves or cut-outs/recesses of the distal plunger 90, thus releasing the delay plunger rod assembly, to the force exerted by the first resilient member 91, in a proximal direction.

The tubular operation member 100 further comprises locking means 104 positioned on the guide means 101, 102 (see FIG. 5). In the illustrated embodiments, the locking means 104 is a flexible tongue having a radial outward protrusion. The locking means 104 is configured to interact with the guide following means 35 i.e. the radially inwards extending protrusion on the distal end of the inner surface of the biased delivery member cover 30 for locking the biased delivery member cover 30 in its most proximal position in order to prevent unintentional interaction with the delivery member 61 after the medicament has been delivered and when the user removed the device from the delivery site.

Figures 6A, 6B, 6C:
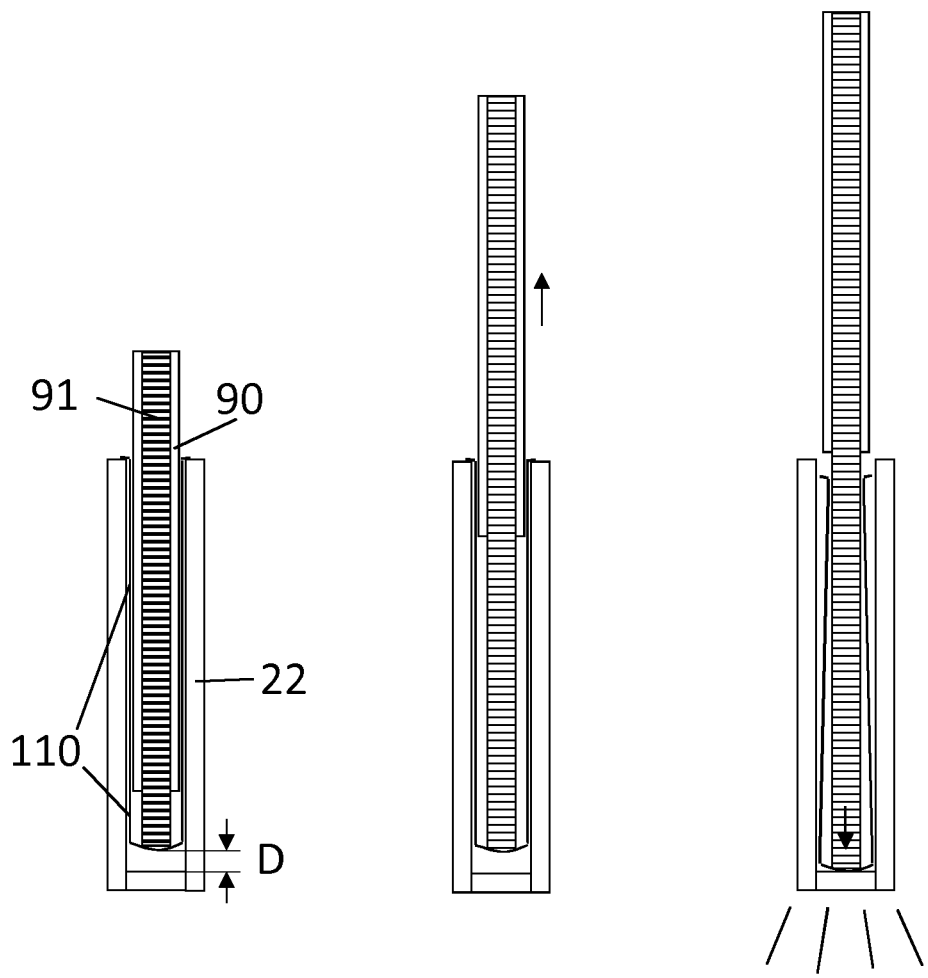
FIG. 6a-FIG. 6c shows a side view of the signal generating member in operation.

FIG. 6a-FIG. 6c illustrates simplified side views of the signal generating member in operation. In the figures are shown the tubular extension part 22 that partly encloses the distal plunger 90 and the signal generating member 110. The first resilient member 91 is enclosed between the distal plunger 90 and the signal generating member 110. More specifically the first resilient member has a first end abutting a proximal end wall 92 of the distal plunger and a second end abutting the transversal wall 112 of the signal generating member.

In FIG. 6a the medicament delivery device 1 is ready for use, wherein the signal generating member 110 is at a predetermined distance "D" from the inner distal surface of the tubular extension part 22.

In FIG. 6b the delivery procedure is initiated and the distal plunger 90 moves in the proximal direction such that the proximal plunger 96 (not shown) forces the stopper 83 (not shown) to expel the medicament via the delivery member 61. When the distal end of the distal plunger 90 has passed the proximal part of the signal generating member 110, the arms 111 of the signal generating member 110 flex inwards allowing the signal generating member 110 to move in the distal direction under exertion of the force of the first resilient member, resulting in a sound, and/or a tactile signal and/or a visual signal being generated when the signal generating member 110 contacts the inner distal surface of the tubular extension part 22. This is illustrated by FIG. 6c.

Figures 7, 8:
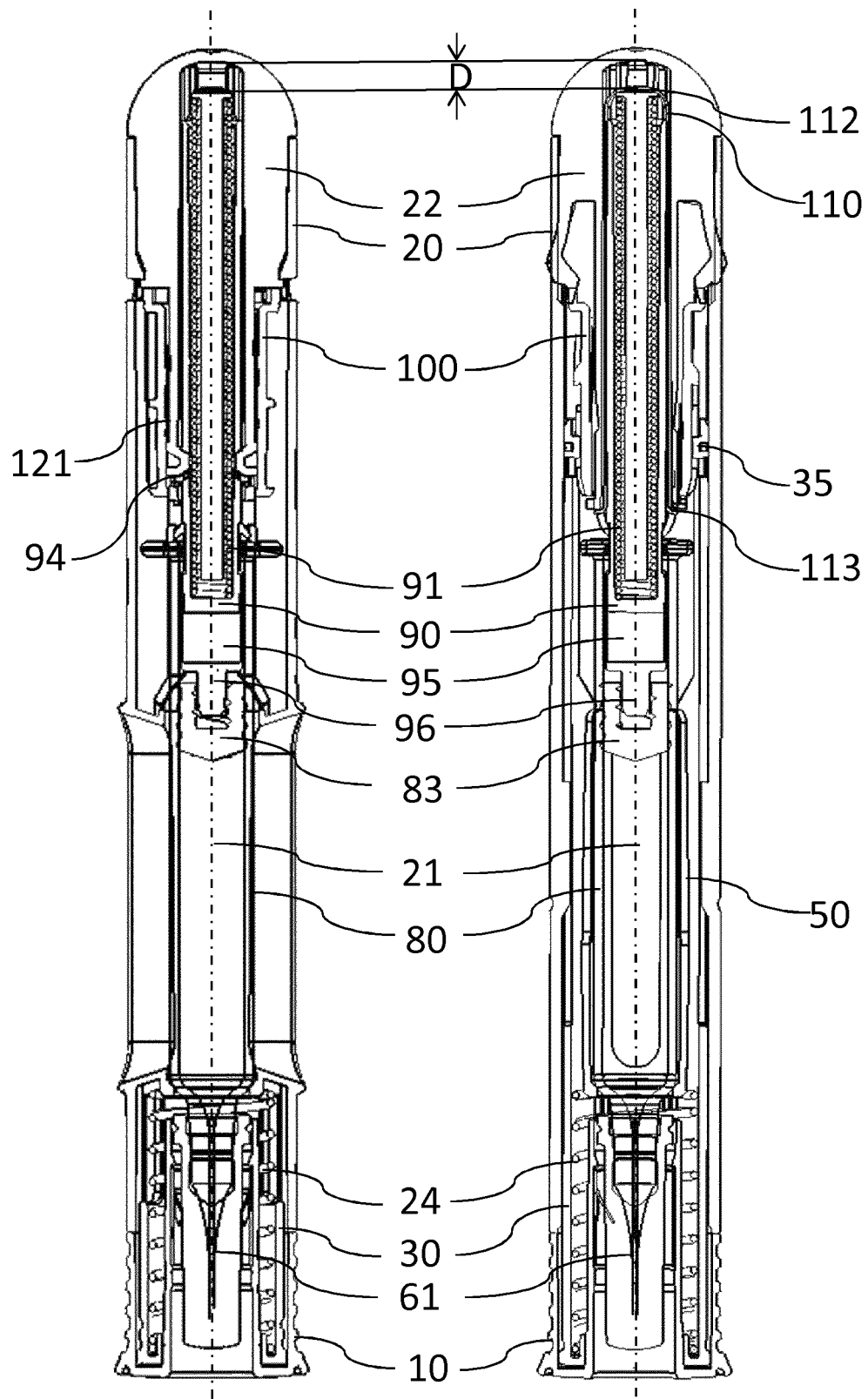
FIG. 7 illustrates a cross-sectional view of the medicament delivery device in an initial, non-activated, state. The sectional plane being perpendicular to the longitudinal axis of the device.
FIG. 8 illustrates a cross-sectional view of the medicament delivery device of FIG. 7 in an initial, non-activated, state. The sectional plane being parallel to the longitudinal axis of the device.

FIG. 7 and FIG. 8 illustrate when the medicament delivery device is in an initial state. In the figures the cap 10 is still attached to the medicament delivery device. The container 80 is arranged within the medicament delivery device having a predetermined volume of medicament and also provided with a delivery member 61 at its proximal end and a stopper 83 at its distal end. The second resilient member 24 is arranged in the proximal end of the medicament delivery device applying a force to the biased delivery member cover 30 in the proximal direction. The proximal plunger 96 has a proximal end in contact with the stopper 83. The distal plunger 90 encloses, at least partly, the first resilient member 91 which is adapted to apply a force to the delay plunger rod assembly in the proximal direction. The distal part of the distal plunger 90 is arranged in the tubular extension part 22 in combination with the signal generating member 110. In the most distal part of the medicament delivery device 100 is indicated the distance "D", i.e. the "signal-generating" distance between the distal part of the signal generating member 110 and the inner distal surface of the tubular extension part 22.

When the medicament delivery is made, the delay plunger rod assembly forces the stopper 83 to expel all medicament from the container 80 through the delivery member 61. The distal part of the distal plunger rod 90 passes by the proximal part of the sound generating member 110 such that the arms 111 are allowed to move inwards due to the pre-tension of the arms. The signal generating member 110 is released and is moved thereby in the distal direction generating a signal, typically a sound, when hitting the inner surface of the tubular extension part 22.

The operation of the medicament delivery device 1 will now be described in more detail. In the pre-tensioned state, the holding means 121 are engaged to the engaging means 94 and are held in such engagement by the inner surface of the tubular operation member 100 for holding the first resilient member 91 pre-tensioned within the distal plunger 90. The second resilient member 24 is forcing the biased delivery member cover 30 towards the proximal end such that the delivery member 61 is covered. When the cap 10 is removed the biased delivery member cover 30 is in its most proximal position and the medicament delivery device 1 is ready for use. The biased delivery member cover 30 is forced in the distal direction by pressing the biased delivery member cover 30 against a delivery site. The guide following means 35 is moved along the guide means 101,102 achieving an anticlockwise rotation of the tubular operation member 100, seen from the distal end, such that the releasing means 105 of the tubular operation member 100 is positioned over the holding means 121 of the tubular extension part 22, allowing the holding means 121 to flex radially outward such that the holding means 121 is disengaged from the engaging means 94 releasing the delay plunger rod assembly. The delay plunger rod assembly is moved in a proximal direction under the force exerted by the first resilient member 91 such that the delay plunger rod assembly displaces the stopper within the medicament container and the medicament is delivered through the delivery member. After the medicament has been completely delivered, the distal plunger 90 exits the tubular extension part 22 such that the signal generating means 110 is released from the tubular extension part 22 and moved in a distal direction by a remaining force of the first resilient member 91. A signal is generated informing the user that the delivery is completed and that the device can be removed from the delivery site. When the medicament delivery device is removed from the delivery site, the biased delivery member cover 30 is forced in the proximal direction, by means of the second resilient member 24. The locking means 104 (see FIG. 5), positioned on the guide means 101, 102 of the tubular operation member 100 interacts with the guide following means 35 when the guide following means 35 is moved over locking means 104 such that the biased delivery member cover 30 is locked i.e. prevented from being distally displaced in relation to the housing.

According to the main aspect of the invention, it is the delay plunger rod assembly that enhances the reliability with which the device provides complete medicament delivery followed by a reliable audible and/or tactile and/or visible confirmation to the user that the delivery has been completed. Said delay plunger rod assembly being configured such that it eliminates the effect of component variable tolerances. The delay means 95*a* (see FIG. 8) is a high-viscous fluid or an expanded polymer e.g. an expanded plastic. The distal plunger is positioned at least partially within or around the proximal plunger and such that said distal plunger is axially movable in relation to said proximal plunger. The aperture is positioned on a wall surface of the distal plunger 90, preferably on a proximal end wall 92 of the distal plunger 90 or on a wall surface 90*a* of the proximal plunger or forms a gap between the distal and proximal plunger, such as an annular gap 90*b* between the distal plunger and the wall surface of the proximal plunger.

When the delay plunger rod assembly is released, the distal plunger 90 starts to exert a force on the delay means. In one exemplary embodiment, the delay means which is a high-viscous fluid contained within the chamber 95, is in fluid communication with the inner space of the distal plunger via the aperture which extends through the proximal end wall 92 of the distal plunger 90 (not shown). As mentioned above, the aperture may be positioned on a wall surface of the proximal plunger, or forms a gap between the distal and proximal plunger, such as an annular gap between the distal plunger and the wall surface of the proximal plunger. When the delay means is a high-viscous fluid, the viscosity of said fluid and the dimensions of the aperture must be chosen such that capillary action does not cause the high-viscous fluid to wick through the aperture. The high-viscous fluid must remain within the chamber 95 by surface tension until it is forcibly expelled through the aperture by a force exerted against the high-viscous fluid by the distal plunger 90. Upon release of the delay plunger rod assembly, the force released by the first resilient member 91 is applied to the distal plunger 90 and thereby to the proximal plunger 96 through the high-viscous fluid included in the chamber 95 such that the proximal plunger 96 acts against the stopper 83 of the medicament container 80, causing the stopper 83 to advance such that the medicament is expelled through the delivery member 61. Due to the rate of force applied by the first resilient member 91 on the distal plunger 90, the high-viscous fluid included in the chamber 95 initially acts as a solid material. Therefore, as the stopper 83 is displaced, the high-viscous fluid included in the chamber does not immediately flow out through the aperture. The continued application of force causes the high-viscous fluid to start flowing out of the chamber 95 through the aperture. Once the stopper 83 reaches the end of its displacement, the force of the first resilient member 91 continues to act against the distal plunger 90. The distal plunger, therefore, continues to transfer the force exerted by the first resilient member 91 to the proximal plunger 96 through the high-viscous fluid contained within the chamber. Delivery of the medicament is completed as the delay plunger rod assembly drives the stopper 83 into the proximal end of the medicament container. However, the dimension of the aperture and the type and volume of fluid included in the chamber are chosen such that, even after delivery of the medicament is completed, an amount of high-viscous fluid remains within the chamber and the release of the signal generating member 110 is thereby delayed. The design of the delay plunger rod assembly and of the rest of the device, therefore, works to ensure that the signal generating member is released after delivery of the medicament is completed. After delivery of the medicament is completed, the first resilient member 91 continues exerting the force causing the distal plunger 90 to continue its travel, resulting in the continued expelling of high-viscous fluid from the chamber. The continued travel of the distal plunger 90 allows the signal generating member to be released. As the signal generating member 110 is released, part of the remaining force is used to move the signal generating member.

The chamber needs to contain a compensatory surplus of high-viscous fluid. Otherwise component tolerances may prevent the release of the signal generating member if the chamber is emptied before the medicament is completely delivered. The delay plunger rod assembly will remain stationary, and thus the signal generating member will fail to be released. By including a surplus of high-viscous fluid within the chamber the distal plunger is allowed to continue proximal movement within the chamber until the signal generating member is released, even when components tolerances hinder actuation of the releasable signal generating member and require that the distal plunger travel a greater distance than anticipated to actuate the releasable signal generating member.

When the delay means is an expanded plastic, some air is enclosed in the expanded plastic. Upon release of the delay plunger rod assembly, the force released by the first resilient member 91 is applied to the distal plunger 90 and thereby to the proximal plunger 96 through the expanded plastic included in the chamber 95 such that the proximal plunger 96 acts against the stopper 83 of the medicament container 80, causing the stopper 83 to advance such that the medicament is expelled through the delivery member 61. Due to the rate of force applied by the first resilient member 91 on the distal plunger 90, the expanded plastic included in the chamber 95 initially acts as a solid material. Therefore, as the stopper 83 is displaced, the continued application of force causes the expanded plastic to be compressed. Once the stopper 83 reaches the end of its displacement, the force of the first resilient member 91 continues to act against the distal plunger 90. The distal plunger, therefore, continues to transfer the force exerted by the first resilient member 91 to the proximal plunger 96 through the expanded plastic contained within the chamber. Delivery of the medicament is completed as the delay plunger rod assembly drives the stopper 83 into the proximal end of the medicament container. However, the material, structure and size of expanded plastic included in the chamber are chosen such that, even after delivery of the medicament is completed, the release of the signal generating member 110 is delayed. The design of the delay plunger rod assembly, and of the rest of the device, therefore works to ensure that the signal generating member is released after delivery of the medicament is completed. After delivery of the medicament is completed, the first resilient member 91 continues exerting the force causing the distal plunger 90 to continue its travel, resulting in the continued compression of the expanded plastic. The continued travel of the distal plunger 90 allows the signal generating member to be released. As the signal generating member 110 is released, part of said remaining force is used to move the signal generating member.

To account for component tolerances it is important to select the properties of the expanded plastic, e.g. material, structure and size, such that some continued travel of the distal plunger is ensured after complete delivery of the medicament. This is because component tolerances may otherwise hinder actuation of the releasable signal generating member and require that the distal plunger travel a greater distance than anticipated to actuate the releasable signal generating member.

It is to be understood that embodiments described above and shown in the drawings are to be regarded only as non-limiting examples of the present invention and that the invention may be modified within the scope of the appended patent claims.

The invention claimed is:

1. A medicament delivery device, comprising:
 a housing having a distal end and a proximal end and configured to receive a medicament container containing a fixed amount of medicament and a delivery member for delivering the medicament;
 a drive mechanism configured to exert pressure on the medicament container to automatically deliver the medicament;
 a hold and release mechanism interactively connected to the drive mechanism for holding the drive mechanism in a pre-tensioned state;
 a biased delivery member cover positioned at least partially within the housing and axially movable within the housing, the cover being interactively connected to the hold and release mechanism such that, when the cover is pressed against a delivery site, the hold and release mechanism releases the drive mechanism from the pre-tensioned state;
 a signal generating member releasably connected to the hold and release mechanism and interactively connected to the drive mechanism for generating at least one of an audible, tactile, and visual signal indicating that the medicament has been completely delivered;
 wherein the drive mechanism comprises a first resilient member and a delay plunger rod assembly; the delay plunger rod assembly comprises a proximal plunger, a distal plunger, a chamber formed between the proximal and the distal plungers, an aperture, and a delay device in the chamber, where the delay plunger rod assembly moves proximally when released from the hold and release mechanism;
 wherein the distal plunger and proximal plunger are configured such that each plunger can move relative to the other plunger prior to and after the release of the drive mechanism,
 wherein the delay device is a volume of viscous fluid,
 wherein the aperture is an annular gap between outside wall surfaces of the proximal and distal plungers, where the annular gap is configured to accept a portion of the viscous fluid as the distal plunger and proximal plunger move relative to each other, and
 wherein the annular gap is sized and the volume of the viscous fluid in the chamber is selected such that an amount of the viscous fluid remains within the chamber after the fixed amount of the medicament is delivered through the delivery member so that release of the signal generating member is delayed until after the proximal plunger stops moving proximally relative to the medicament container.

2. The medicament delivery device of claim 1, wherein the distal plunger is positioned at least partially within or around the proximal plunger such that the distal plunger is axially movable in relation to the proximal plunger.

3. The medicament delivery device of claim 1, wherein the drive mechanism exerts pressure on the medicament container by directly exerting pressure on a stopper within the medicament container.

4. The medicament delivery device of claim 1, wherein the first resilient member is arranged pre-tensioned within the distal plunger.

5. The medicament delivery device of claim 1, wherein the hold and release mechanism comprises a tubular extension part fixedly connected to the distal end of the housing and a tubular operation member interactively connected to the tubular extension part and to the biased delivery member cover.

6. The medicament delivery device of claim 5, wherein the tubular operation member comprises a guide device interactively connected to guide a following device of the biased delivery member cover, and a releasing device configured for interactive connection to a holding device of the tubular extension part.

7. The medicament delivery device of claim 6, wherein the distal plunger is at least partially and axially movable within the tubular extension part, and the distal plunger comprises an engaging device interactively connected to the holding device of the tubular extension part.

8. The medicament delivery device of claim 7, wherein the signal generating member comprises an elongated U-shaped bracket arranged between the tubular extension part and the distal plunger, the signal generating member comprises a transversal wall and two longitudinally extending flexible arms having angled support members extending radially outward, and the support members rest on an annular proximal end of the tubular extension part when the drive mechanism is in the pre-tensioned state.

9. The medicament delivery device of claim 8, wherein the first resilient member has a first end abutting a proximal end wall of the distal plunger and a second end abutting the transversal wall of the signal generating member.

10. The medicament delivery device of claim 9, wherein the transversal wall of the signal generating member is arranged at a predetermined distance from an inner distal surface of the tubular extension part when the drive mechanism is in the pre-tensioned state.

11. The medicament delivery device of claim 7, wherein the releasing device comprises a longitudinally extending groove on an inner surface of the tubular operation member, and the holding device of the tubular extension part comprises a resilient tongue having a radially inward protrusion.

12. The medicament delivery device of claim 11, wherein the engaging device comprises a groove or cut-out/recess on an outer surface of the distal plunger configured to receive the radially inward protrusion of the resilient tongue.

13. The medicament delivery device of claim 12, wherein the guide device comprises at least one tracking groove on an outer surface of the tubular operation member, and the following device comprises a radially inwardly extending protrusion on a distal end of the inner surface of the biased delivery member cover such that the radially inwardly extending protrusion is guided within the at least one tracking groove, thereby forcing the tubular operation member to rotate when the biased delivery member cover is distally moved, whereby the resilient tongue of the tubular extension part is flexed radially outward into the longitudinally extending groove on the inner surface of the tubular operation member and the radially inward protrusion of the resilient tongue is disengaged from the outer surface of the distal plunger such that the drive mechanism is released from the pre-tensioned state.

14. The medicament delivery device of claim 13, wherein an audible signal confirms that the fixed amount of medicament is delivered when the drive mechanism is released and the distal end of the distal plunger has passed the angled support members of the signal generating member such that the longitudinally extending flexible arms are flexed radially inward, thereby enabling the signal generating member to move the predetermined distance in the distal direction by a remaining force exerted by the first resilient member, whereby the transversal wall of the signal generating member hits an inner distal surface of the tubular extension part.

15. The medicament delivery device of claim 14, wherein the transversal wall of the signal generating member comprises a distally extending protrusion, and the distal surface of the tubular extension part comprises a through-hole, such that when the transversal wall of the signal generating member hits the inner distal surface of the tubular extension part, the distally extending protrusion passes through the through-hole and extends distally a predetermined distance over an outer surface of the tubular extension part, thereby generating the tactile signal.

16. The medicament delivery device of claim 15, wherein the distally extending protrusion has at least one of a brightness and a color that is different from a brightness and color of a rest of the device, thereby generating the visual signal.

17. The medicament delivery device of claim 1, wherein the device is an injection device and the delivery member is a needle or a pen needle.

18. A medicament delivery device, comprising:
   a housing having a distal end and a proximal end and configured to receive a medicament container containing a fixed amount of medicament and a delivery member for delivering the medicament;
   a drive mechanism configured to exert pressure on the medicament container to automatically deliver the medicament;
   a hold and release mechanism interactively connected to the drive mechanism for holding the drive mechanism in a pre-tensioned state;
   a biased delivery member cover positioned at least partially within the housing and axially movable within the housing, the cover being interactively connected to the hold and release mechanism such that, when the cover is pressed against a delivery site, the hold and release mechanism releases the drive mechanism from the pre-tensioned state;
   a signal generating member releasably connected to the hold and release mechanism and interactively connected to the drive mechanism for generating at least one of an audible, tactile, and visual signal indicating that the medicament has been completely delivered;
   wherein the drive mechanism comprises a first resilient member and a delay plunger rod assembly; the delay plunger rod assembly comprises a proximal plunger, a distal plunger, a chamber formed between the proximal and the distal plungers and a delay device in the chamber;
   wherein the distal plunger and proximal plunger are configured such that each plunger can move relative to the other plunger prior to and after the release of the drive mechanism,
   wherein the delay device is a piece of expanded plastic comprising enclosed air,
   wherein the piece of expanded plastic is sized such that the distal plunger will compress the expanded plastic within the chamber to allow the distal plunger to move relative to the proximal plunger after the fixed amount of the medicament is delivered through the delivery member so that release of the signal generating member is delayed until after the proximal plunger stops moving proximally relative to the medicament container.

* * * * *